United States Patent [19]

Plummer

[11] Patent Number: 4,596,892

[45] Date of Patent: Jun. 24, 1986

[54] METHANAMINE INTERMEDIATES TO INSECTICIDAL 2,2'-BRIDGED [1,1'-BIPHENYL]-3-YLMETHYL CARBOXAMIDES

[75] Inventor: Ernest L. Plummer, Yardley, Pa.

[73] Assignee: FMC Corporation, Philadelphia, Pa.

[21] Appl. No.: 725,024

[22] Filed: Apr. 19, 1985

Related U.S. Application Data

[60] Continuation of Ser. No. 598,125, Apr. 9, 1984, abandoned, which is a division of Ser. No. 409,751, Aug. 19, 1982, Pat. No. 4,493,844.

[51] Int. Cl.$^4$ ............................................. C07C 87/28
[52] U.S. Cl. .................................. 564/387; 564/142; 564/180; 564/385
[58] Field of Search ......................................... 564/387

[56] References Cited

U.S. PATENT DOCUMENTS

| 3,403,157 | 9/1968 | Humber et al. | 564/387 X |
| 3,639,423 | 2/1972 | Winter et al. | 564/387 X |
| 3,649,692 | 3/1972 | Humber | 564/387 |

FOREIGN PATENT DOCUMENTS 4021418  9/1965  Japan ................................... 564/387

Primary Examiner—Robert V. Hines
Attorney, Agent, or Firm—R. L. Hansen; H. R. Ertelt

[57] ABSTRACT 2,2'-Bridged[1,1'-biphenyl]-3-ylmethyl carboxamides and insecticidal compositions containing these carboxamides are useful for the control of a broad range of insects and acarids.

1 Claim, No Drawings

METHANAMINE INTERMEDIATES TO INSECTICIDAL 2,2'-BRIDGED [1,1'-BIPHENYL]-3-YLMETHYL CARBOXAMIDES

This application is a continuation of application Ser. No. 598,125, filed Apr. 9, 1984 and now abandoned which is a division of Ser. No. 409,751, filed 8/19/82, now U.S. Pat. No. 4,493,844.

This invention pertains to the field of bioaffecting compositions; more specifically, it pertains to novel carboxamide insecticides, processes and intermediates thereto, insecticidal and acaricidal compositions containing the novel carboxamides, and to the use of the compositions for controlling insects and acarids.

Pyrethrins, which are naturally occurring organic esters, have long been of interest as insecticides. Many synthetic pyrethroids are more effective than the natural pyrethrins, and recent modifications have overcome a chronic pyrethrin problem - instability to air and light.

The carboxylic acid moiety in the aforesaid esters is often a 2,2-dimethylcyclopropane-1-carboxylic acid with various substituents in the 3-position. Many variations in the alcohol moiety of the aforesaid esters have been investigated also. The structural features of pyrethroid insecticides have been reviewed, e.g., Chem. Soc. Rev., 7, 473 (1978). U.S. patents 4,130,657; 4,214,004 and 4,329,518 disclose that [1,1'-diphenyl]-3-ylmethyl carboxylates wherein the carboxylic acid moiety contains a pyrethroid acid residue exhibit insecticidal and acaricidal activity.

It has now been found that insecticidal and acaricidal carboxamides result when a 2,2'-bridged[1,1'-biphenyl]-3-yl-methanamine moiety is coupled with a pyrethroid carboxylic acid moiety. Like the earlier esters, several of the new carboxamides are capable of both geometrical and optical isomerism, the biological activity varying somewhat according to the specific isomer. The term "2,2'-bridged[1,1'-biphenyl]-3-ylmethyl carboxamide" employed herein is intended to include generically all optical and geometrical isomers of the named compound and mixtures thereof. The terms "halo," "halogen," or "halide" mean fluorine, chlorine or bromine. The term "lower" modifying alkyl or alkoxy means $C_1$ to $C_6$, preferably $C_1$ to $C_4$.

Insecticidal and acaricidal 2,2'-bridged[1,1'-biphenyl]-3-ylmethyl carboxamides of this invention are represented by Formula I

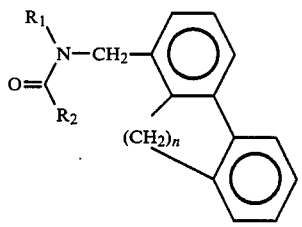

wherein n is 2–4, $R_1$ is hydrogen or lower alkyl, and $R_2$ is a pyrethroid acid residue, i.e., the residue of a carboxylic acid which forms an insecticidal ester with 3-phenoxybenzyl alcohol.

Attractive pyrethroid acid residues include 3-(2,2-dihaloethenyl)-2,2-dimethylcyclopropyl, especially 3-(2,2-dichloroethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(1,2,2,2-tetrabromoethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 4-chloro-α-(1-methylethyl)phenylmethyl; 4-difluoromethoxy-α-(1-methylethyl)phenylmethyl; 3-(1,3-butadienyl)-2,2-dimethylcyclopropyl; 2,2-dimethyl-3-(oximinomethyl)cyclopropyl; 2-(2-chloro-α,α,α-trifluoro-p-toluidino)-3-methylbutyl; 3-(2,3,4,5-tetrahydro-2-oxothien-3-ylidenemethyl)-2,2-dimethylcyclopropyl; 2,2-dichloro-1-(4-ethoxyphenyl)cyclopropyl; 4-halo-α-(1-cyclopropyl)phenylmethyl; spiro[2,2-dimethylcyclopropane-1,1'-[1H]-indene]-3-yl; spiro[3-(2,2-dichloroethenyl)-cyclopropane-1,1'-cyclohexane]-2-yl; spiro[3-(2,2-dichloroethenyl)cyclopropane-1,1'-cyclobutane]-2-yl; 3-phenyl-2,2-dimethylcyclopropyl; 3-(4-halophenyl)-2,2-dimethylcyclopropyl; 3-(4-methoxyphenyl)-2,2-dimethylcyclopropyl; 3-(4-ethoxyphenyl)-2,2-dimethylcyclopropyl; and 3-(3,4-methylenedioxyphenyl)-2,2-dimethylcyclopropyl.

Among the aforesaid carboxamides it is preferred that n be 3 or 4, that $R_1$ be hydrogen, and that $R_2$ be either 3-(2,2-dichloroethenyl)-2,2-dimethylcyclopropyl or 3-(2-chloro-3,3,3-trifluoro-1-propenyl)-2,2-dimethylcyclopropyl. An espcially attractive insecticide and acaricide is N-(6,7-dihydro-5H-dibenzo-[a,c]cyclohepten-4-yl)methyl 3-(2chloro-3,3,3-trifluoro-1-propenyl)-2,2-dimethylcyclopropanecarboxamide, wherein n is 3, particularly the cis isomer.

Also within the contemplation of this invention are insecticidal and acaricidal compositions comprising an insecticidally or acaricidally effective amount of 2,2'-bridged[b 1,1'-biphenyl]-3-ylmethyl carboxamide in admixture with an agriculturally acceptable carrier and a method of controlling insects or acarids which comprises applying to the locus where control is desired an insecticidally or acaricidally effective amount of 2,2'-bridged[1,1'-biphenyl]-3-ylmethyl carboxamide.

When the locus is soil, e.g. soil in which agricultural crops are planted, it may be advantageous to incorporate the 2,2'-bridged[1,1'-biphenyl]-3-ylmethyl carboxamide into the soil. This is especially effective in controlling certain pests, such as southern corn rootworm. N-(6,7-dihydro-5H-dibenzo[a,c]cyclohepten-4-yl)methyl 3-(2-chloro-3,3,3-trifluoro-1-propenyl)-2,2-dimethylcyclopropanecarboxamide, for example, is especially active against southern corn rootworm when employed in this manner.

The 2,2'bridged-[1,1'-biphenyl]-3-ylmethyl carboxamides of this invention are prepared by reaction between a carbonyl halide, e.g. a chloride, $R_2COCl$, wherein $R_2$ is a pyrethroid acid residue, and an appropriate 2,2'-bridged[1,1'-biphenyl]-3-methanamine. Alternatively, they are prepared by reacting the carboxamide anion, $R_2CONR_1^{(-)}$, wherein $R_1$ is hydrogen or lower alkyl, and $R_2$ is a pyrethroid acid residue, said anion being formed from the amide and a strong base, e.g., NaOH or KOH/DMSO, NaH, or an alkyl lithium, with an appropriate 2,2'-bridged[1,1'-biphenyl]-3-ylmethyl compound wherein the benzylic carbon atom carries a leaving group which is readily displaced by said carboxamide anion; e.g., see Synthesis, 266 (1971). Suitable leaving groups are known in the art and include, for example, halogen, especially bromine and chlorine; carboxylate, especially acetate; sulfonate, e.g.,

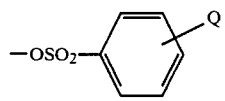

where Q is halogen, especially bromine, $C_1$-$C_6$ alkyl, e.g., p-toluenesulfonate, nitro, or hydrogen, and —O—$SO_2C_RH_SF_T$ where R is 1–4, e.g., methanesulfonate, and S and T are independently 0–9; and —$NR_3X$, where R may be $C_1$-$C_6$ alkyl, and X may be halogen, sulfonate, or other readily available anion. 2,2'-Bridged[1,1'-biphenyl]-3-ylmethyl compounds with such leaving groups are described in copending application Ser. No. 368,608, filed Apr. 15, 1982 and now U.S. Pat. No. 4,451,484, incorporated herein by reference.

3-(2,2-Dichloroethenyl)- and 3-(2,2-dibromoethenyl)-2,2-dimethylcyclopropanecarboxylic acid and corresponding carbonyl chlorides are obtained by methods disclosed in U.S. Pat. No. 4,024,163. Carbonyl chlorides or corresponding salts wherein R is 2,2,3,3-tetramethylcyclopropyl, 2,2-dichloro-3,3-dimethylcyclopropyl, 3-cyclopentylidenemethyl-2,2-dimethylcyclopropyl, and 4-chloro-α-(1-methylethyl)phenylmethyl, are disclosed in *Agr. Biol. Chem.*, 31, 1143 (1967), *Agr. Biol. Chem.*, 38, 1511 (1974), U.S. 3,679,667, and *Agr. Biol. Chem.*, 39, 267 (1975), respectively. The 3-(2-methyl-1-propenyl)-2,2-dimethylcyclopropyl, 3-(1,2-dibromo-2,2-dichloroethyl)-2,2-dimethylcyclopropyl, and the set of 3-(2-chloro-3,3,3-trifluoro-1-propenyl)-2,2-dimethylcyclopropyl, 3-(3-chloro-2,3,3-trifluoro-1-propenyl)-2,2-dimethylcyclopropyl, and 3-(2,3-dichloro-3,3-difluoro-1-propenyl)-2,2-dimethylcyclopropyl acid residues are described in *Agr. Biol. Chem.*, 28, 27 (1961), and U.S. 4,179,575, respectively. The 4-difluoromethoxy-α-(1-methylethyl)phenylmethyl acid residue is disclosed in *Agr. Biol. Chem.*, 38, 881 (1974), while *Pestic. Sci.*, 7, 499 (1976) describes 3-(1,3-butadienyl)-2,2-dimethylcyclopropyl. U.S. Pat. No. 3,922,269, *Pestic. Sci.*, 11, 224 (1980), and U.S. Pat. No. 3,842,177 disclose 2,2-dimethyl-3-(oximinomethyl)cyclopropyl, 2-(2-chloro-α,α,α-trifluoro-p-toluidino)-3-methylbutyl, and 3-(2,3,4,5-tetrahydro-2-oxothien-3-ylidenemethyl)-2,2-dimethylcyclopropyl, respectively. *Nature*, 272, 734 (1978) describes 2,2-dichloro-1-(4-ethoxyphenyl)cyclopropyl. The spiro[2,2-dimethylcyclopropane-1,1'-[1H]indene]-3-yl acid residue appears in *Adv. Pestic. Sci., Plenary Lect. Symp. Paper Int. Congr. Pestic. Chem.*, 4th 1978, 2, p. 190. The remaining spiro acid residues are disclosed in "Synthetic Pyrethroids," ACS Symposium Series No. 42, Washington, D.C., 1977, page 37, while the 3-phenyl and substituted phenyl-2,2-dimethylcyclopropyl acid residues have been described by Farkas and Novak, *Coll. Czech. Chem. Comm.*, 25, 1815 (1960). The 4-halo-α-(1-cyclopropyl)phenylmethyl acid residues appear in *Abstracts, Fourth International Congress of Pesticide Chemistry*, Zurich, 1978. The 3-(1,2,2,2-tetrabromoethyl)-2,2-dimethylcyclopropyl acid residue is described in U.S. Pat. No. 4,231,932. These disclosures are also incorporated herein by reference.

The pure cis or trans cyclopropanecarboxamides are prepared either by reacting pure cis or pure trans cyclopropanecarboxylic acid derivatives with appropariate 2,2'-bridged [1,1'-biphenyl]-3-methanamines or -3-ylmethyl compounds, or by separating cis,trans mixtures using chromatographic techniques.

2,2'-Bridged[1,1'-biphenyl]-3-methanamines, which are intermediate in the preparation of the insecticidal carboxamides, are novel compositions of matter and are also within the scope of this invention. These intermediates are described by Formula II

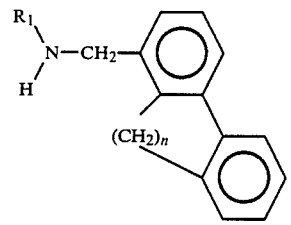

wherein n is 2–4 and $R_1$ is hydrogen or lower alkyl. Intermediates within the scope of this invention include, for example, 6,7-dihydro-5H-dibenzo[a,c]cyclohepten-4-methanamine, (N-methyl) 6,7-dihydro-5H-dibenzo[a,c]cyclohepten-4-methanamine, and 5,6,7,8-tetrahydrodibenzo[a,c]cycloocten-4-methanamine.

Preparation of specific compounds within the scope of this invention is illustrated below. Unless otherwise indicated, all temperatures are in degrees Celsius and pressures are in millimeters of mercury. Proton chemical shifts, taken from nmr spectra in CDCl$_3$, are reported in ppm with respect to tetramethylsilane.

EXAMPLE A 6,7-Dihydro-5H-dibenzo[a,c]cyclohepten-4-methanamine

Under a dry nitrogen atmosphere a stirred mixture of 6,7-dihydro-5H-dibenzo[a,c]cyclohepten-4-carbonitrile (1.0 gram, 0.0045 mole) in ethanol (20 ml) and 10% aqueous sodium hydroxide (20 ml) was heated at reflux for two days. The mixture was cooled and poured into dilute hydrochloric acid (150 ml). The resulting mixture was extracted with five 100 ml portions of methylene chloride and the extracts combined. The combined extracts were washed with two 100 ml portions of water, dried over anhydrous magnesium sulfate and filtered. The solvent was removed from the filtrate by distillation under reduced pressure to leave 6,7-dihydro-5H-dibenzo[a,c]cyclohepten-4-carboxamide as a white solid (1.1 grams, mp>250°).

Under a dry nitrogen atmosphere 6,7-dihydro5H-dibenzo[a,c]-cyclohepten-4-carboxamide (0.78 gram, 0.0033 mole) was reacted with lithium aluminum hydride (0.2 gram, 0.0053 mole) in tetrahydrofuran (100 ml) to produce a white solid. The solid was recrystallized from a solution of diethyl ether and petroleum ether to provide 6,7-dihydro-5H-dibenzo[a,c]cyclohepten-4-methanamine (0.11 g, mp 200°–210°). The solvent was removed from the mother liquor to yield an additional 0.5 gram of the amine.

EXAMPLE B (N-methyl) 6,7-dihydro-5H-dibenzo[a,c]cyclohepten-4-methanamine

A solution of 6,7-dihydro-5H-dibenzo[a,c]cyclohepten-4-carbonyl chloride (2.3 grams, 0.009 mole) in benzene (40 ml) was stirred under an atmosphere of dry methylamine gas. A white solid formed within 20 minutes. The mixture was stirred for two days at room temperature, then filtered. The filter cake was rinsed with hot benzene (200 ml), then dried to yield (N-methyl) 6,7-dihydro-5H-dibenzo[a,c]cyclohepten-4-carboxamide (2.1 grams).

Treatment of (N-methyl) 6,7-dihydro-5H-dibenzo[a,c]cyclohepten-4-carboxamide (2.1 grams, 0.0083 mole) with lithium aluminum hydride (0.52 gram, 0.014 mole) in tetrahydrofuran (75 ml) and diethyl ether (50 ml) yielded (N-methyl) 6,7-dihydro-5H-dibenzo[a,c]cyclohepten-4-methanamine (2.0 grams).

EXAMPLE C 5,6,7,8-Tetrahydrodibenzo[a,c]cycloocten-4-methanamine

Reduction of 5,6,7,8-tetrahydrodibenzo[a,c]cycloocten-4-carbonitrile (3.9 grams, 0.017 mole) with lithium aluminum hydride (1.3 grams, 0.033 mole) in tetrahydrofuran (60 ml) produced 5,6,7,8-tetrahydrodibenzo[a,c]cycloocten-4-methanamine as a solid (4.0 grams). The nmr and ir spectra were consistent with the proposed structure.

EXAMPLE I

N-(6,7-Dihydro-5H-dibenzo[a,c]cyclohepten-4-yl)methyl cis-3-(2-Chloro-3,3,3-trifluoro-1-propenyl)-2,2-dimethylcyclopropanecarboxamide A solution containing 6,7-dihydro-5H-dibenzo[a,c]cyclohepten-4-methanamine (0.5 gram, 0.0022 mole) and benzene (40 ml) was added dropwise to a stirred solution of cis-3-(2-chloro-3,3,3-trifluoro-1-propenyl)-2,2-dimethylcyclopropanecarboxylic acid chloride (0.75 gram, 0.0029 mole) and pyridine (1.0 gram, 0.013 mole) in benzene (20 ml). The resulting mixture was stirred at room temperature for approximately 16 hours, poured into water and the total extracted with three 100 ml portions of diethyl ether. The combined extracts were washed with a 10% aqueous sodium carbonate solution (100 ml) followed by two 50 ml portions of water. The washed extracts were dried over anhydrous magnesium sulfate, and filtered. The solvent was evaporated from the filtrate under reduced pressure leaving a yellow residue. This residue was purified by column chromatography on silica gel, elution with benzene:diethyl ether (3:1), to yield N-(6,7-dihydro-5H-dibenzo[a,c]cyclohepten-4-yl)methyl cis-3-(2-chloro-3,3,3-trifluoropropenyl)-2,2-dimethylcyclopropanecarboxamide as a colorless solid (0.85 gram, mp 65°–70°).

Analysis: Calc'd for $C_{25}H_{25}ClF_3NO$: C 67.04; H 5.63; Found: C 67.83; H 6.19.

Nmr: 1.26(s,3H); 1.39(s,3H); 2.04–2.80(m,8H); 4.59–4.62 (d,2H); 5.88–6.08(m,1H); 7.36–7.80(m,8H).

Other 2,2'-bridged[1,1'-biphenyl]-3-ylmethyl carboxamides of this invention were similarly prepared and are listed below, together with physical properties and elemental analyses (found).

EXAMPLE II (N-methyl) N-(6,7-dihydro-5H-dibenzo[a,c]cyclohepten-4-yl)methyl cis-3-(2,2-dichloroethenyl)-2,2-dimethylcyclopropanecarboxamide mp 55°–60°.
Analysis: 69.83% C; 6.32% H.
Nmr: 1.07–1.27(m,6H); 1.73–2.77(m,8H); 2.97(s,3H); 4.70 (s,2H); 6.23–6.57(m,1H); 7.07–7.37(m,7H).

EXAMPLE III (N-methyl) N-(6,7-dihydro-5H-dibenzo[a,c]cyclohepten-4-yl)methyl cis-3-(2-chloro-3,3,3-trifluoropropenyl)-2,2-dimethylcyclopropanecarboxamide mp 55°–60°.
Analysis: 66.45% C; 5.65% H.
Nmr: 1.12–1.33(m,6H); 1.77–2.67(m,8H); 2.90–3.03(d,3H); 4.70(s,2H); 6.90–7.07(m,8H).

EXAMPLE IV

N-(5,6,7,8-Tetrahydrodibenzo[a,c]cycloocten-4-yl)methyl cis-3-2-chloro-3,3,3-trifluoropropenyl)-2,2-dimethylcyclopropanecarboxamide, liquid.

Analysis: 68.56% C; 5.63% H.
Nmr: 1.13–2.97(m,10H); 1.30–1.37(m,6H); 4.50–4.60(d,2H); 5.63–5.97(m,1H); 7.07–7.37(m,8H).

EXAMPLE V

N-(5,6,7,8-Tetrahydrodibenzo[a,c]cycloocten-4-yl)methyl-trans-3-(2,2-dichloroethenyl)-2,2-dimethylcyclopropanecarboxamide mp 153°–155°.
Analysis: 68.32% C; 6.09% H.
Nmr: 1.17–3.00(m,16H); 4.50–4.60(dd,2H); 5.57–5.71(d,1H); 5.60–5.70(m,1H); 7.10–7.37(m,7H).

EXAMPLE VI

N-(5,6,7,8-Tetrahydrodibenzo[a,c]cycloocten-4-yl)methyl 1R-cis-3-(2,2-dichloroethenyl)-2,2-dimethylcyclopropanecarboxamide, liquid.

Analysis: 69.94% C; 6.29% H.
Nmr: 1.23–3.07(m,16H); 4.56–4.63(d,2H); 5.60–6.00(m,1H); 6.37–6.60(dd,1H); 7.13–7.40(m,7H).

In the normal use of the insecticidal and acaricidal carboxamides of the present invention, the carboxamides usually will not be employed free from admixture or dilution, but ordinarily will be used in a suitable formulated composition compatible with the method of application and comprising an insecticidally or acaricidally effective amount of 2,2'-bridged-[1,1'-biphenyl]-3-ylmethyl carboxamide. The carboxamides of this invention, like most pesticial agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present coarboxamides may be applied, for example, as sprays, dusts, or granules to the area where pest control is desired, the type of application varying of course with the pest and the environment. Thus, the carboxamides of this invention may be formulated as granules of large particle size, as powdery dusts, as wettable powders, as emulsified concentrates, as solutions, and the like.

Granules may comprise porous or nonporous particles, such as attapulgite clay or sand, for example, which serve as carriers for the carboxamides. The granule particles are relatively large, a diameter of about 400–2500 microns typically. The particles are either impregnated with the carboxamide from solution or coated with the carboxamide, adhesive sometimes being employed. Granules generally contain 0.05–10%, preferably 0.5–5%, active ingredient as the insecticidally effective amount.

Dusts are admixtures of the carboxamides with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects and acarids contains 1 part of 2,2'-bridged[1,1'-biphenyl]-3-ylmethyl carboxamide, such as N-(6,7-dihydro-5UMS/H/ -dibenzo[a,c]cyclohepten-4-yl)methyl cis-3-(2-chloro-3,3,3-trifluoro-1-propenyl)-2,2-dimethylcyclopropanecarboxamide, and 99 parts of talc.

The carboxamides of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5–50% 2,2'-bridged[1,1'-biphenyl]-3-ylmethyl carboxamide, such as N-(6,7-dihydro-5$\underline{H}$-dibenzo[a,c]cyclohepten-4-yl)methyl cis-3-(2-chloro-3,3,3-trifluoropropenyl)-2,2-dimethylcyclopropanecarboxamide, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects and acarids contains 1.5 parts each of sodium lignosulfonate and sodium laurylsulfate as wetting agents, 25 parts of n-(6,7-dihydro-5H-dibenzo[a,c]cyclohepten-4-yl)methyl cis-3-(2-chloro-3,3,3,-trifluoropropenyl)-2,2-dimethylcyclopropanecarboxamide, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the carboxamide with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal and acaricidal composition.

Other useful formulations include simple solutions of the active ingredient in a solvent in which it is completely soluble at the desired concentration, such as acetone or other organic solvents.

An insecticidally or acaricidally effective amount of 2,2'-bridged [1,1-biphenyl]-3-ylmethyl carboxamide in an insecticidal or acaricidal composition diluted for application is normally in the range of about 0.001% to about 8% by weight. Many variations of spraying and dusting compositions known in the art may be used by substituting the carboxamides of this invention into compositions known or apparent to the art.

The insecticidal or acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally or acaricidally effective amount of 2,2'-bridged [1,1'-biphenyl]-3-ylmethyl carboxamide be applied to the locus where control is desired. When the locus is soil, e.g., soil in which agricultural crops are planted, the active compound may be applied to and optionally incorporated into the soil. For most applications, an insecticidally or acaricidally effective amount will be about 75 to 4000 g per hectare, preferably 150 g to 3000 g per hectare.

The insecticidal and acaricidal activity of the 2,2'-bridged [1,1'-biphenyl]-3-ylmethyl carboxamides, whose preparation is described above, were evaluated as follows:

The activity was evaluated in topical application to southern armyworm (*Spodoptera eridania*), Mexican bean beetle (*Epilachna varivestis*), large milkweed bug (*Oncopeltus fasciatus*), and southern corn rootworm (*Diabrotica undecimpunctata*). Two replicates of 10 test larvae per replicate were placed in 9 cm petri dishes, each lined with a piece of filter paper and a food source. On the second or third dorsal thoracic segment of each larva was placed a 1 microliter droplet containing the desired amount of the test compound in acetone. The toxic effect of the compound was determined 24 hours after application. An insect was considered dead if it could no longer right itself and move in an oriented pattern. The results of these tests appear in Table 1.

The compounds were also tested in foliar applications at various concentrations in aqueous solutions containing 10% acetone and 0.25% emulsifier. The plants (English fava bean for pea aphid and pinto bean for the remaining species) were placed on a revolving turntable in a hood, and the test solutions were applied with a sprayer. The test solutions were applied to the upper and lower surfaces of the plant leaves while the turntable revolved 10 times (5 for upper surface and 5 for lower surface). The total spray time was approximately one minute, and the leaves were covered to runoff. In every case the lowest rate was applied first and the highest rate last. The plants were then allowed to dry. The treated leaves were removed and placed in 240 ml or 480 ml wax treated containers. Ten individuals of the appropriate species were placed in each container and the container capped. Mortality was read 48 hours post-treatment unless otherwise noted. Two replicates of ten individuals were made at each rate. Foliar evaluation used southern armyworm (*Spodoptera eridania*), Mexican bean beetle (*Epilachna varivestis*), pea aphid (*Acyrthosiphon pisum*), cabbage looper (*Trichoplusia ni*) and twospotted spider mite (*Tetranychus urticae*). The results of the foliar tests appear in Table 2.

TABLE 1

Topical Evaluation

| Compound | Rate (ng) | Insects[a] (% Kill) | | | |
|---|---|---|---|---|---|
| | | MBB | MBW | SAW | SCR |
| Ex. I | 5000 | 100 | 100 | 100 | |
| Ex. II | 5000 | 45 | 0 | 0 | |
| Ex. III | 5000 | 0 | 0 | 0 | |
| Ex. IV | 2500 | 90 | 65 | 0 | |
| | 500 | | | | 100 |
| | 200 | 20 | | | |
| Ex. V | 2500 | 0 | 0 | 0 | |
| | 500 | | | | 0 |
| Ex. VI | 2500 | 0 | 0 | 0 | |
| | 500 | | | | 0 |

[a]MBB = Mexican bean beetle
MWB = milkweed bug
SAW = southern armyworm
SCR = southern corn rootworm

TABLE 2

Folier Evaluation

| Compound | Rate (ppm) | Insects[a] (% Kill) | | | | |
|---|---|---|---|---|---|---|
| | | MBB | PA | SAW | CL | TSM |
| Ex. I | 64 | 100 | 80 | 80 | | 44 |
| | 48 | | | 60 | | |
| | 32 | 70 | 75 | 25 | | |
| | 24 | | | 20 | | |
| | 20 | | | | 100 | |
| | 16 | 30 | 65 | 0 | 95 | 0 |
| | 8 | 15 | 15 | | 55 | |
| | 4 | 0 | 10 | | 50 | |
| | 1 | | | | 20 | |
| Ex. II | 500 | | 40 | 0 | | 0 |
| | 128 | | 55 | | | |
| | 96 | | 30 | | | |
| | 80 | | 20 | | | |
| | 64 | 65 | 10 | 0 | | |
| | 48 | | 0 | | | |
| Ex. III | 500 | | 100 | 0 | | 0 |
| | 128 | | 55 | | | |
| | 96 | | 20 | | | |
| | 64 | 15 | 15 | 0 | | |
| Ex. IV | 1250 | | 100 | 0 | | 0 |
| | 64 | 40 | 0 | | 75 | |
| | 16 | 0 | 0 | | 25 | |
| Ex. V | 1250 | | 0 | 20 | | 0 |
| | 64 | 0 | 80 | | 100 | |
| | 16 | 0 | 0 | | 55 | |
| Ex. VI | 1250 | | 100 | 100 | | 0 |
| | 80 | | 55 | | | |
| | 64 | | 35 | | 85 | |
| | 48 | | 30 | | | |
| | 32 | | 25 | | 80 | |
| | 16 | | 5 | | 40 | |
| | 8 | | | | 0 | |

[a]MBB = Mexican bean beetle
PA = pea aphid
SAW = southern armyworm
CL = cabbage looper
TSM = twospotted spider mite

I claim:
1. 6,7-Dihydro-5H-dibenzo[a,c]cyclohepten-4-methanamine.

* * * * *

UNITED STATES PATENT AND TRADEMARK OFFICE
CERTIFICATE OF CORRECTION

PATENT NO. : 4,596,892

DATED : June 24, 1986

INVENTOR(S) : Ernest L. Plummer

It is certified that error appears in the above—identified patent and that said Letters Patent is hereby corrected as shown below:

Column 1, line 29," [1,1'-diphenyl]"should read [1,1'-biphenyl]--.
Column 7, line 17, "N-(6,7-dihydro-5UMS/H-dibenzo" should read --N-(6,7-dihydro-5H-dibenzo--. Column 7, line 44, "25 parts of n-(6,7-dihydro-5H" should read --25 parts of N-(6,7-dihydro-5H--.

Signed and Sealed this

Seventeenth Day of February, 1987

Attest:

DONALD J. QUIGG

Attesting Officer     Commissioner of Patents and Trademarks